United States Patent
Shoemaker

(10) Patent No.: US 6,365,590 B1
(45) Date of Patent: Apr. 2, 2002

(54) COMPOUNDS, COMPOSITIONS AND METHODS FOR TREATING ERECTILE DYSFUNCTION

(75) Inventor: James D. Shoemaker, Clayton, MO (US)

(73) Assignee: Saint Louis University, St. Louis, MO (US)

(*) Notice: Subject to any disclaimer, the term of this patent is extended or adjusted under 35 U.S.C. 154(b) by 0 days.

(21) Appl. No.: 09/642,502

(22) Filed: Aug. 18, 2000

Related U.S. Application Data

(60) Continuation-in-part of application No. 09/474,990, filed on Dec. 29, 1999, now abandoned, which is a division of application No. 09/084,849, filed on May 26, 1998, now Pat. No. 6,124,461.

(51) Int. Cl.$^7$ .................. C07D 239/72; A61F 31/495
(52) U.S. Cl. ............. 514/252.17; 514/567; 514/559; 514/560; 514/626; 544/283; 554/222; 564/193
(58) Field of Search ............. 514/252.7, 567, 514/559, 560, 626; 544/252.17; 564/193; 554/222

(56) References Cited

U.S. PATENT DOCUMENTS

| | | | |
|---|---|---|---|
| 4,801,587 A | 1/1989 | Voss et al. | 514/288 |
| 5,145,852 A | 9/1992 | Virag | 514/248 |
| 5,242,391 A | 9/1993 | Place et al. | 604/60 |
| 5,447,912 A | 9/1995 | Gerstenberg et al. | 514/12 |
| 5,482,039 A | 1/1996 | Place | 128/653.1 |
| 5,552,157 A | 9/1996 | Yagi et al. | 424/450 |
| 5,565,466 A | 10/1996 | Gioco et al. | 514/280 |
| 5,567,706 A | 10/1996 | Gavras | 514/280 |
| 5,583,144 A | 12/1996 | Kral | 514/321 |
| 5,648,350 A | 7/1997 | DeLignieres et al. | 514/178 |
| 5,658,936 A | 8/1997 | Kifor et al. | 514/381 |

FOREIGN PATENT DOCUMENTS

| | | |
|---|---|---|
| DE | 195 26 984 A | 1/1997 |
| EP | 0 357 581 A | 3/1990 |

OTHER PUBLICATIONS

Hellstrom et al. "A double–bind, placebo–controlled evaluation of the erectile response to transurethral alprostadil"; *Urology* 1996:48(6):851–6.

Padma–Nathan et al. "treatment of men with erectile dysfunction with transurethral alprostadil" Medicated Urethral System for Erection (MUSE) Study Group, *N. Eng. J. Med.* Jan. 1997; 336(1):1–7.

Purvis et al. "Determinants of satisfactory rigidity after intracavernosal injection with prostaglandin E1 in men with erectile failure" *Int. J. Impot. Res.* 1996;8(1):9–16.

Hedlund et al. "Pharmacotherapy in erectile dysfunction agents for self–injection programs and alternative application models" *Scand. J. Urol Nephrol. Suppl.* 1996;179:129–38.

Schramek et al. "Intracavernous injection of prostaglandin $E_1$ plus procaine in the treatment of erectile dysfunction" *J. Urol* 1994;152:1108–1110.

Kattan, S. "Double–blind randomized crossover study comparing intracorporeal prostaglandin E1 with combination of prostaglandin E1 and lidocaine in the treatment of organic impotence" *Urology* Jun. 1995;45(6):1032–6.

Wolfson et al. "Intraurethral prostaglandin E–2 cream: a possible alternative treatment for erectile dysfunction" *Urology* 1993;42:73–5.

Schouman et al. "Suppression of prostaglandin E–1 induced pain by dilution of the drug with lidocaine before intracavernosal injection" *J. Urology* 1992; 148:1226, letter.

Tanaka, T. "Papaverine hydrochloride in peripheral blood and the degree of penile erection" *J. Urology* 1990;143:1135–7.

Cawello et al. "Pharmacokinetics of prostaglandin E1 and its main metabilites afer Intracavernous injection and shortterm infusion of prostaglandin E1 in patients with erectile dysfunction" *J. Urology* Oct. 1997; 158(4):1403–7.

Sundaram et al. "Long–term follow–up of patients receiving injection therapy for erectile dysfunction" *Urology* Jun. 1997; 49(6):932–5.

Soderahl et al. "Intracavernosal drug–induced erection therapy versus external vacuum devices in the treatment of erectile dysfunction" *Br. J. Urol.* Jun. 1997;79(6):952–7.

McMahon, CG "Nonsurgical treatment of cavernosal venous leakage" *Urology* Jan. 1997;49(1):97–100.

Hellstrom et al. "A double–blind, placebo–controlled evaluation of the erectile response to transurethral alprostadil" *Urology* Dec. 1996;48(6):851–6.

Chen et al. "The lowest effective dose of prostaglandin E1 as treatment for erectile dysfunction" *J. Urol.* Jan. 1995;153(1):80–1.

National Institutes of Health: Impotence. Consensus Development Conference Statement. *Int. J. Imp. Res.* 1993;5:181.

MacMahon, CG "A comparison of the response to the intracavernosal injection of a combination of papaverine and phentolaime, Prostaglandin E–1 and a combination of all three agents in the management of impotence" *Int. J. Impot. Res.* 1991;3:113.

(List continued on next page.)

Primary Examiner—Zinna Northington Davis
(74) Attorney, Agent, or Firm—Darby & Darby

(57) ABSTRACT

Vasoactive compounds are described for the treatment of erectile dysfunction and impotence. The compounds are reaction products of an anionic or negatively charged vasoactive or erection-inducing component (such as alprostadil) and a cationic or positively charged vasoactive or erection-inducing component (such as prazosin) or a local anesthetic (such as lidocaine). These components are combined as acids and bases to form an organic salt or ionically bonded compound. The compounds have advantageous solubility characteristics and efficacy. A compound of the invention is combined with a pharmaceutical vehicle to form a composition which preferably includes an emulsifier. A local anesthetic and/or androgenic steroids may also be included. Compositions of the invention may also include more than one vasoactive organic salt compound. The composition can be advantageously formulated and administered to allow self-adjusted dosing, while minimizing or preventing overdosing.

18 Claims, 10 Drawing Sheets

OTHER PUBLICATIONS

Shenfeld et al. "Papaverine–phentolamine and prostaglandin E1 versus papaverine–phentolamine alone for intracorporeal injection therapy: a clinical double–blind study" *J. Urol.* Sep. 1995; 154(3):1017–9.

Lue et al. "Impotence [editorial]" *J. Urol.* Jul. 1995; 154(1):85.

Virag, R. "Intracavernous injection of papaverine for erectile failure" Lancet 1982;2:938.

Brindley, GS "Cavernosal alpha–blockage: a new technique for investigating and treating erectile impotence" *Br. J. Psychiatry* 1983;143:332.

Furlow, W.L. "Prevalence of impotence in the United States" *Med. Apsects Hum. Sex* 1985 19:13–8.

Flynn et al. "Long–term follow–up of patients with erectile dysfunction commenced on self injection with intracavernosal papaverine with or with phentolamine" *J. Urology* Oct. 1996; 78(4):628–631.

Lea et al. "Intracavernous Alprostadil A Review of its Pharmacodynamic and Pharmacokinetic Properties and Therapeutic Potential in Erectile Dysfunction" *Drugs & Aging* Jan. 1996 ;8(1):56–74.

Vaidyanathan et al. "Myocardial infarction associated with intra–cavernosal administration of alprostadil in a patient with spinal cord injury and paraplegia" [letter] *Spinal Cord* Dec. 1996 ;34(12):754–5.

Chiang et al. "Papaverine and Prostaglandin $E_1$ Gel Applications for Impotence" *Ann. Acad. Med. Singapore* Sep. 1995;24(5):767–9.

Kim et al. "Papaverine Topical Gel for Treatment of Erectile Dysfunction" *J. Urol.* Feb. 1995, 153(2):361–5.

Seidmon et al. "The pH Analysis of Papaverine–Phentolamine and Prostaglandin $E_1$ for Pharmacologic Erection" *J. Urology* Jun. 1989; 141:1458–9.

Godschalk et al. "Alkalization Does Not Alleviate Penile Pain Induced by Intracavernous Injection of Prostaglandin E1" *J. Urol.* Sep. 1996; 156(3):999–1000.

Tostain, et al. "Traitement des troubles erectiles par les androgenes: Quand? Comment?, "[Androgen Treatment of Erectile Dysfunction: When? How?] *Progres en Urologie,* vol. 7, pp. 314–319 (1997).

Marin, "Testosterone and Regional Fat Distribution," *Obesity Research,* vol. 3, Suppl., pp. 609s–611s (Nov. 4, 1995).

MUSE description sheet, two pages dated Nov. 1996.

Physician Desk Reference, misc. pp. 864–865 (1997).

Physician Desk Reference, misc. p. 1523 (1997).

Scala et al., "Male Erectile Dysfunction", Feb. 12, 1998.

Gouvier et al., "Timing of Penile Color Flow Duplex Ultrasonography Using a Triple Drug Mixture", *The Journal of Urologies,* vol. 153, pp. 1472–1475 (1995).

Porst, "The Rationale for Prostaglandin E1 in Erectile Failure: A Survey of Worldwide Experience", *The Journal of Urologie,* vol. 155, pp. 802–815 (1996).

Porst, "The Rationale For Prostaglandin E1 in Erectile Failure: A Survey of Worldwide Experience", The Virtual Medical Center, mediconsult.com, pp. 1–3 (date unknown).

Bechara et al., "Prostaglandin E1 Versus Mixture of Prostaglandin E1, Papaverine and Phentolamine in Nonresponders to High Papaverine Plus Phentolamine Doses", *The Journal of Urologie,* vol. 155, pp. 913–914 (1996).

Fallon, "Intracavernous Injection Therapy for Male Erectile Dysfunction", *Urologies Clinics of North America,* vol. 22, No. 4, pp. 833–845 (1995).

Bennett et al., 514 Abstract of: "An Improved Vasoactive Drug Combination For A Pharmacological Erection Program (PEP)", undated.

Sikora et al., 516 Abstract of: "Subjective and Objective Success–Parameters After Dorsal Venous Ligature in Erectile Dysfunction", undated.

Chao et al., excerpt from "Experience with Intracavernosal Tri–Mixture for the Management o Neurogenic Erectile Dysfunction", Medical Center Compounding Pharmacy, Intracorporeal Injections, (two pages) (undated).

Urethra and penis—disorders of function, Chapter 32, pp. 521–523, (unknown author) (origin unknown).

Treating Impotence with Hormones and Drugs, pp. 143–147, (unknown author) (origins unknown).

Injection of the Corpora Cavernosa With Pharmacologic Agents (Papeverine, Phentolamine), pp. 1–4 (1995).

Chemical Abstracts, vol. 125, No. 11, A. Bechara et al., "Prostaglandin E1 versus mixture of prostaglandin E1, papaverine and phentolamine in non–responders to high papaverine plus phentolamine doses", p. 260 (Sep. 9, 1996).

Chemical Abstracts, vol. 130, No. 6, A. Bechara et al.: "Comparative Study of Papaverine Plus Phentolamine versus Prostaglandin E1 in Erectile Dysfunction", p. 73 (Feb. 8, 1999).

Chemical Abstracts, vol. 130, No. 6, Armin Becker et al.: "Oral Phentolamine as Treatment for Erectile Dysfunction", p. 75, (Feb. 8, 1999).

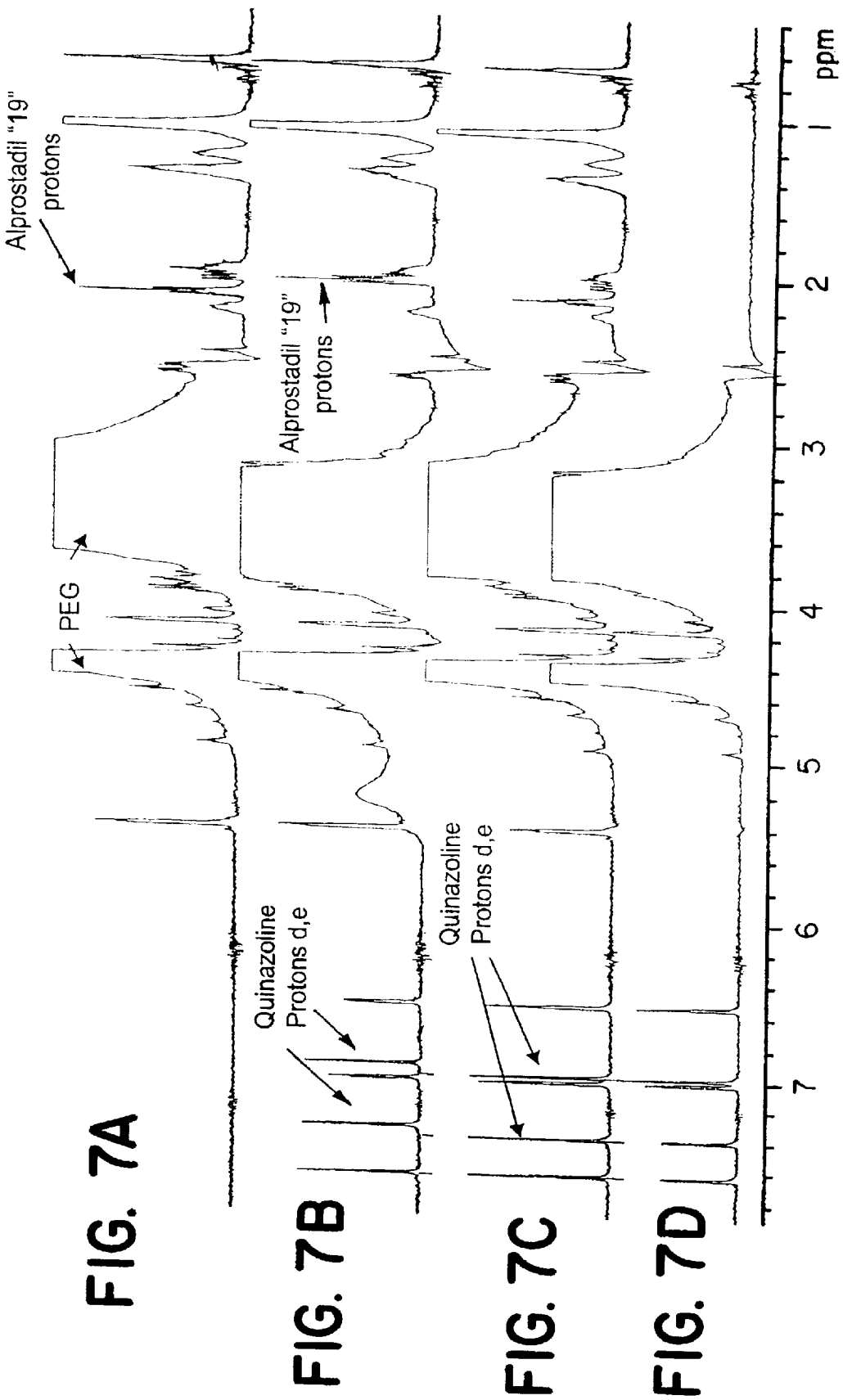

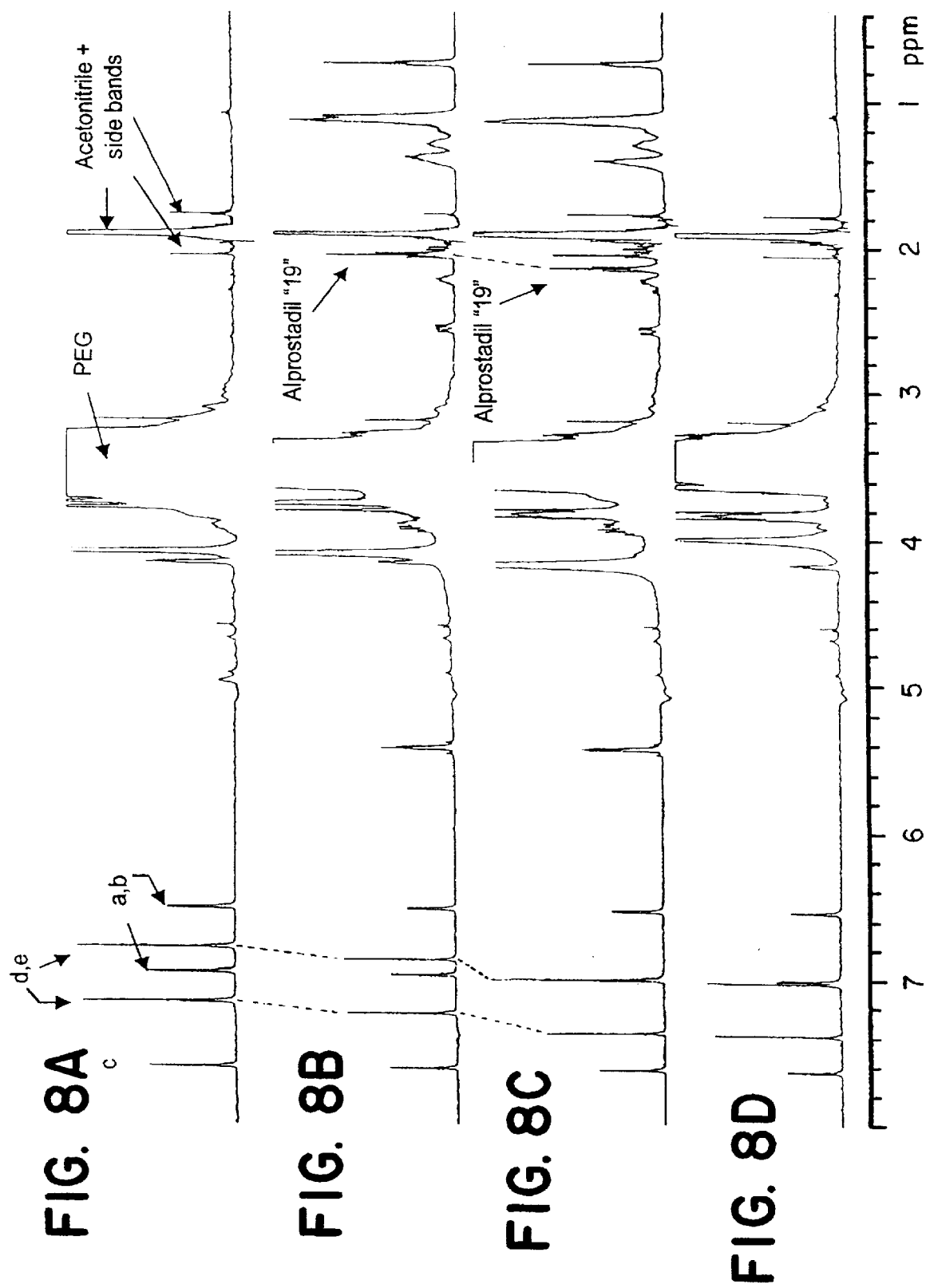

COMPOUNDS, COMPOSITIONS AND METHODS FOR TREATING ERECTILE DYSFUNCTION

This application is a continuation-in-part of U.S. patent application Ser. No. 09/474,990, filed Dec. 29, 1999, now abandoned, which is a division of U.S. patent application Ser. No. 09/084,849, filed May 26, 1998, now issued as U.S. Pat. No. 6,124,461. Both of these prior applications are hereby incorporated by reference.

FIELD OF THE INVENTION

This invention relates to compounds for the treatment of erectile dysfunction, including impotence. In particular, the invention relates to vasoactive compounds and their production, and treatments for impotence and the enhancement of sexual performance in men. The invention also includes a vehicle, delivery system and emulsifier for treating impotence.

BACKGROUND OF THE INVENTION

Erectile dysfunction or impotence is characterized by the inability to achieve or maintain erection or tumescence of the penis. Impotence can be secondary to a wide variety of causes and may be physiological or psychological in origin. This condition is estimated to affect approximately 10–20 million American men chronically, but affects all men occasionally. For example, erection of the penis is inhibited in normal men due to anxiety, exertion or sexual disinterest. Sexual activity includes physical exertion and as men age, the inhibitory effects of exertion may overcome normal arousal mechanisms.

The etiology of chronic impotence may be psychogenic (32%), mixed psychogenic and organic (14%), organic (41%) or anatomical (13%). Organic causes include arterial insufficiency (27%), cavernous leakage (28%), neurological damage (13%), endocrinological defects (2.3%) and Peyronie's disease (13.1%). Govier, F. E. *Timing of Penile Color Flow Duplex Ultrasonography Using a Triple Drug Mixture. J. Urol,* Vol. 153(5) (May 1995), pp.1472–1475. Thus, about 30% of all cases of impotence are primarily vascular in origin.

Compounds which produce or enhance arterial vasodilation or bring about cavernous vein constriction may be successful for the treatment of impotence. See U.S. Pat. Nos. 5,567,706 and 5,583,144, incorporated by reference. Similarly, compounds which counteract inhibitors of erection, such as catecholamines, may also contribute to effectiveness. Compounds which have been used in the pharmacological induction of erection were the vasodilator papaverine and the catecholamine antagonist, phenoxybenzamine. Such compounds may be administered by injection into the corpora cavernosa of the penis. Brindly, G. S. *Cavernosal Alpha-blockage: A New Technique for Investigating and Treating Erectile Impotence, Br J. Psychiatry,* Vol. 143 (1983), pp.332. These compounds are thought to work by mimicking the physiological mechanisms that relax penile smooth muscle.

Erection of the penis may be a self-perpetuating process of three steps: 1) vasodilation; 2) release of endogenous smooth-muscle relaxants; and 3) progression of these effects distal from the initial site of onset. This has been termed the "cascade effect". According to this hypothesis, local induction of vasodilation in the corpus cavernosum may perpetuate itself into full erection of the penis whether or not the original vasodilator diffuses throughout the tissue. Where the concentration of vasoactive drug is highest, there is a local increase in blood flow, an activation of endothelium-mediated relaxing factors such as endothelium-derived nitric oxide, and an enlarging zone of regional smooth muscle relaxation. This "cascade" of a relaxation-inflow-relaxing effect can produce an erection. Support for this hypothesis is found in the observation that high doses of vasoactive drugs are required for erection in impotent patients with endothelial cell dysfunction, such as diabetes and hypercholesterolemia, presumably due to inability of these cells to produce vasodilators. The hypothesis is also supported by the observation that injected vasoactive drugs do not appear to uniformly diffuse from the injection site throughout the corpora of the penis, but are still capable of producing a full erection.

One of the first compounds used successfully for intracavernosal treatment of impotence is papaverine hydrochloride. Papaverine is an opium alkaloid and works as a smooth muscle relaxer possibly by cyclic GMP phosphodiesterase inhibition. It relaxes the musculature of the vascular system of the penis and increases blood flow. The effectiveness of papaverine hydrochloride injection depends on the dose, but has been reported to cause penile hematoma, elevated liver enzymes, priapism and lightheadedness in some patients, particularly if over-used. The free base of papaverine has been tried as a topical agent in the treatment of erectile dysfunction. In concentrations up to 20%, it was not sufficiently effective for clinical use. Kim, E. D. *Papaverine Topical Gel Treatment For Erectile Dysfunction, Urology,* Vol. 133(2)(1995), pp.361–365.

Another compound found effective in treating impotence is phentolamine hydrochloride or phentolamine methane sulfonate (phentolamine mesylate), described in U.S. Pat. No. 2,503,059 incorporated by reference. Phentolamine free base is a nonspecific alpha-adrenergic antagonist and has been successful in inducing penile erection, particularly when used in combination with papaverine. This combination was found to produce greater vasodilation of the arteries of the penis than either phentolamine or papaverine used alone.

Another compound found useful in the treatment of impotence is prostaglandin $E_1$, a naturally occurring compound that acts to increase arterial inflow to the penis and may also restrict venous outflow. Prostaglandin $E_1$ is preferred to other compounds used in injections for the treatment of impotence because it is metabolized locally in the penis and is less likely to cause systemic symptoms such as hypotension. Further, use of prostaglandin $E_1$ has been found to result in a significantly lower incidence of penile hematomas from injections than either papaverine or phentolamine. However, prostaglandin $E_1$ is considerably more expensive than other therapies and causes pain distal from the site of injection.

A synthetic form of prostaglandin $E_1$, alprostadil USP (alprostadil), is a long-chain carboxylic acid with vasodilatory effects. Alprostadil acts to increase arterial inflow to the penis. In vitro studies have shown that alprostadil causes a dose-dependent smooth muscle relaxation in isolated corpus cavernosum and corpus spongiosum preparations. When used in vivo, it is thought that intraurethral alprostadil is absorbed from the urethra, transported throughout the erectile bodies of the penis by way of communicating vessels between the corpus spongiosum and corpus cavernosum, and induces vasodilation of the targeted vascular beds.

Various forms of alprostadil are available on the market, such as CAVERJECT (Upjohn, Kalamazoo, Mich.), which is an injectable form of alprostadil. Another form of alprostadil is MUSE (Vivus, Inc., Menlo Park, Calif.) which is a combination of alprostadil and polyethylene glycol. Intraurethral administration of MUSE has been reported to result in a substantial increase of cavernosal artery diameter and as much as a 10-fold increase in peak systolic flow velocities. Injections of alprostadil have been reported to cause pain, bleeding, hematomas and scar tissue leading to Peyronie's Disease in some patients.

Urethral inserts or suppositories have been developed as an alternative to intracavernosal injection therapy. For example, U.S. Pat. No. 5,242,391, incorporated by reference, describes a device for the urethral insertion of a pellet containing alprostadil. The device has been reported to be effective about 65% of the time in doses of 125 to 1000 micrograms of alprostadil. However, urethral inserts do not appear to be as successful in treating impotence as intracavernosal injections.

The urethra is sensitive to irritants. There have been some reports that local anesthetic agents such as procaine and lidocaine can relieve some of the irritation upon intracavernosal injection. Schouman, M., *Suppression of Prostaglandin E-1 Induced Pain By Dilution of the Drug With Lidocaine Before Intracavernosal Injection, J. Urology*, Vol 148 (1992), pp.1266.

Androgenic steroids may also have a role in induction of erection, especially for patients with hypogonadism. Dihydrotestosterone has been administered transdermally, but has never been administered intraurethrally. Because dihydrotestosterone is fat-soluble, this may be a reasonable route of delivery. Tostain, J., *Androgen Treatment of Erectile Dysfunction: When?How? Progres en Urologie*, Vol. 7 (1997), pp.314–319.

Combinations of papaverine, phentolamine and alprostadil have been shown to be effective in treating impotence. For example, intracavernosal injections of this three-way combination, known as "tri-mix", can be more effective in treating impotence with fewer side effects than papaverine, phentolamine or alprostadil used alone. Together, these compounds appear to act synergistically to increase arterial inflow, dilate sinusoidal smooth muscles, and restrict venous outflow, all promoting erectile activity with greater success and in smaller doses than single compound therapies. An example of a dosage combination for tri-mix is 10 micrograms of alprostadil, 500 micrograms of phentolamine and 15 mg of papaverine. Dosing of tri-mix preparations has not been standardized.

Agents for the formation of cationic liposomes are known to increase the solubility of substances they contain in cell membranes. Cationic phospholipids have been described for this purpose, such as phosphatidylethanolamine and phosphatidylcholine. Medium chain fats are useful for the solubilization of chemicals in membranes because they are both fat and water soluble. Therefore, diacylphosphatidylcholine, where the acyl groups are medium chain fats, may be especially efficacious as an emulsifier to aid the uptake of organic compounds by cell membranes. Dilauroylphosphatidylcholine has been disclosed as an ingredient in a composition to form cationic liposomes, for example, in U.S. Pat. No. 5,552,157, incorporated by reference. In the invention, cationic liposomes may form spontaneously when a composition as described is mixed with moisture from the urethra.

SUMMARY OF THE INVENTION

The effectiveness of compositions for the transurethral treatment of impotence depends largely on the chemical nature of the active ingredients and their ability to traverse cell membranes of the urethra and increase blood flow into the corpora cavernosa of the penis. An important factor is fat solubility, which allows diffusion across cell membranes. The invention provides compounds which can be used alone or together for the treatment of erectile dysfunction, particularly impotence. The invention is concerned with compounds that are useful in the treatment of impotence, particularly when delivered to the urethra. The compounds are formed as a complex or reaction product of components in which the lipophobic properties of one or more components are mitigated by formation of the compound. Formation of a compound, as opposed to a mixture of components, can be detected for example by NMR spectroscopy. Methods of making and using these compounds are also disclosed, as is an improved vehicle and delivery system.

The compounds of the invention each comprise a complex or reaction product of an anionic or negatively charged vasoactive or erection-inducing component and a cationic or positively charged vasoactive or erection-inducing component. These components are combined as acids and bases to form compounds which are believed to be organic salts or ionically bonded compounds. One or more compounds of the invention can be used in a composition for treating erectile dysfunction, with or without other ingredients. In a preferred composition, a compound of the invention is combined with a pharmaceutical vehicle and preferably includes an emulsifier. An emulsifier is provided to increase solubility in the mucous membrane of the urethra and can be a form of lecithin, or a compound of the general formula diacylphosphatidylcholine, where the "acyl" portion might include any medium-to-long chain carboxylic acids of from six to twelve carbons in length. The preferred emulsifier is dilauroylphosphatidylcholine. A local anesthetic may also be included. Preferred anesthetics are lidocaine, also called xylocaine. Preferred compositions may also include more than one compound of the invention.

The compounds of the invention can be represented by the formula:

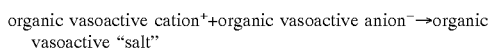

organic vasoactive cation$^+$+organic vasoactive anion$^-$→organic vasoactive "salt"

The organic cation is selected from any of the following vasoactive compounds as the free base: phentolamine, papaverine, hydralazine, ketanserin, delquamine (delaquamine), n trazaodone, yohimbine, linsidomine, molsidomine, ifenprodil, piribedil, dipyramidole, minoxidil, phenoxybenzamine, prazosin, terazocin, doxazocin, sildenafil or moxisylyte (moxisylate), or local anesthetics such as procaine or lidocaine free base. The organic anion is selected from any of the following as free acids: vasoactive eicosanoids such as the free acid alprostadil (prostaglandin $E_1$), prostaglandin $E_0$, (13,14-dihydroprostaglandin $E_1$), dinoprostone (prostaglandin $E_2$), epoprostenol (prostacyclin, $PGI_2$) and other prostaglandins; or other vasoactive anions such as nitroprusside.

One compound of the invention is a combination of alprostadil (an acid) and lidocaine (a base). Another compound of the invention is a combination of alprostadil and prazosin (a base). Each compound of the invention is believed to form as an ionically bonded salt of its acid and base components. The compounds have the surprising property of high solubility in drug delivery vehicles and lipids, and can easily diffuse across transitional epithelia cells of the urethra. Also, the compounds are benign and effective without undesirable side effects. In a preferred embodiment, compounds of the invention are formulated with an emulsifier, preferably dilauroylphosphatidylcholine, with or without a local anesthetic, such as lidocaine, also known as xylocaine.

The compounds and compositions of the invention can be administered by intraurethral injection or by application to the surface of the penis in the form of a topical composition or agent for transdermal delivery to the urethra.

The compounds and compositions of the invention provide improved solubility, and allow for self-adjusted dosage while preventing overdose problems. In one embodiment, a composition comprising a complex of alprostadil with each of lidocaine and prazosin provides for lower effective doses of alprostadil than in other therapies. This is thought to be achieved by increasing the absorption efficiency, by delivering the composition intraurethrally and by providing a more lipophillic composition which can cross membrane barriers more easily. Thus, alprostadil complexes with lidocaine to form the compound lidocaine alprostadilate. Alprostadil complexes with prazosin to form the compound prazosin alprostadilate.

Surprisingly, the new compounds have synergistic erection-inducing properties, and require significantly less alprostadil component than previously known intraurethral or multi-component intracavernosal therapies. The lidocaine and prazosin moieties are thought to provide an anesthetic effect and alpha-adrenergic blockage, respectively. Additionally, they each neutralize the acidity of alprostadil, rendering the resulting compounds, which can be thought of as salt complexes, fat soluble. Compositions of the invention, comprising one or more compounds formed as the reaction product of acid and base components having erection-inducing properties, have a neutral pH of about 6.0. Alprostadil is acidic, and known alprostadil compositions have an acid pH of about 4.5–5.2 (e.g. for various dosages of MUSE). Further, the anhydrous formulation of lidocaine alprostadilate and prazosin alprostadilate in the presence of an emulsifier, such as dilauroylphosphatidylcholine, ensures that the compounds remain at a neutral pH and in solution as an emulsion upon contact with the neutral aqueous environment of the urethra. The micro droplets which make up this emulsion may directly solubilize in the transitional epithelium of the urethra or the constituents may disassociate by an ion exchange process.

The active ingredients of the composition are provided at significantly lower concentrations than in the prior art. For example, preferred embodiments of the invention provide an effective amount of alprostadil, as lidocaine alprostadilate or prazosin alprostadilate, that can be one-tenth the concentration of alprostadil provided in the commercially available preparation known as MUSE. Consequently, even if compounds or compositions of the invention are self-administered beyond recommended dosage or schedule, the holding capacity of the human urethra will limit dosage to a safe amount. Further, in contrast to needle injections, which deposit the active drug at only one point, intraurethral administration allows diffusion across the urethral membrane all along the line of its path through the cavernosa. This may be another factor which explains why smaller doses of lidocaine and prazosin are effective at inducing erection intraurethrally in comparison to intracavernosally.

BRIEF DESCRIPTION OF THE DRAWINGS

In the drawings, which constitute part of this application, embodiments and data demonstrating various features of the invention are set forth as follows:

FIG. 7a is the NMR spectra of alprostadil in $d_2O$:PEG10% deutero DMSO;

FIG. 7b is the NMR spectra of prazosin free base and alprostadil in $d_2O$ 10% deutero DMSO;

FIG. 7c is the NMR spectra of prazosin hydrochloride and alprostadil in 10% $d_2O$:PEG 10% deutero DMSO;

FIG. 7d is the NMR spectra of prazosin hydrochloride in 10% $d_2O$:PEG:10% deutero-DMSO;

FIG. 8a is the NMR spectra of prazosin and NaOH in PEG;

FIG. 8b is the NMR spectra of prazosin HCl and NaOH in PEG and alprostadil;

FIG. 8c is the NMR spectra of prazosin HCl in PEG and alprostadil;

FIG. 8d is the NMR spectra of prazosin HCl in PEG ;

DETAILED DESCRIPTION OF THE INVENTION

Figure 1:
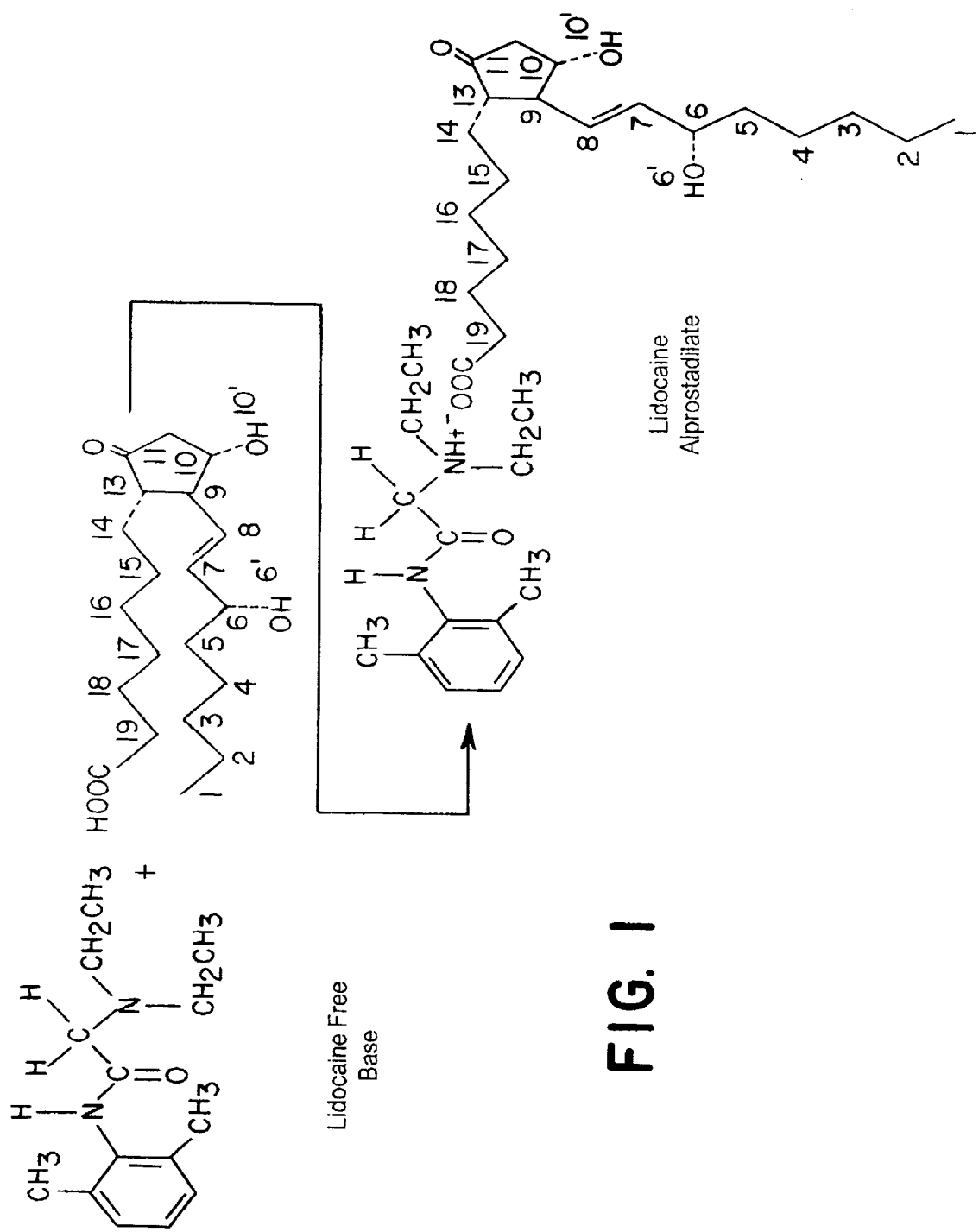
FIG. 1 is a reaction scheme for the synthesis of lidocaine alprostadilate.
Figures 2A, 2B, 2C, 2D:
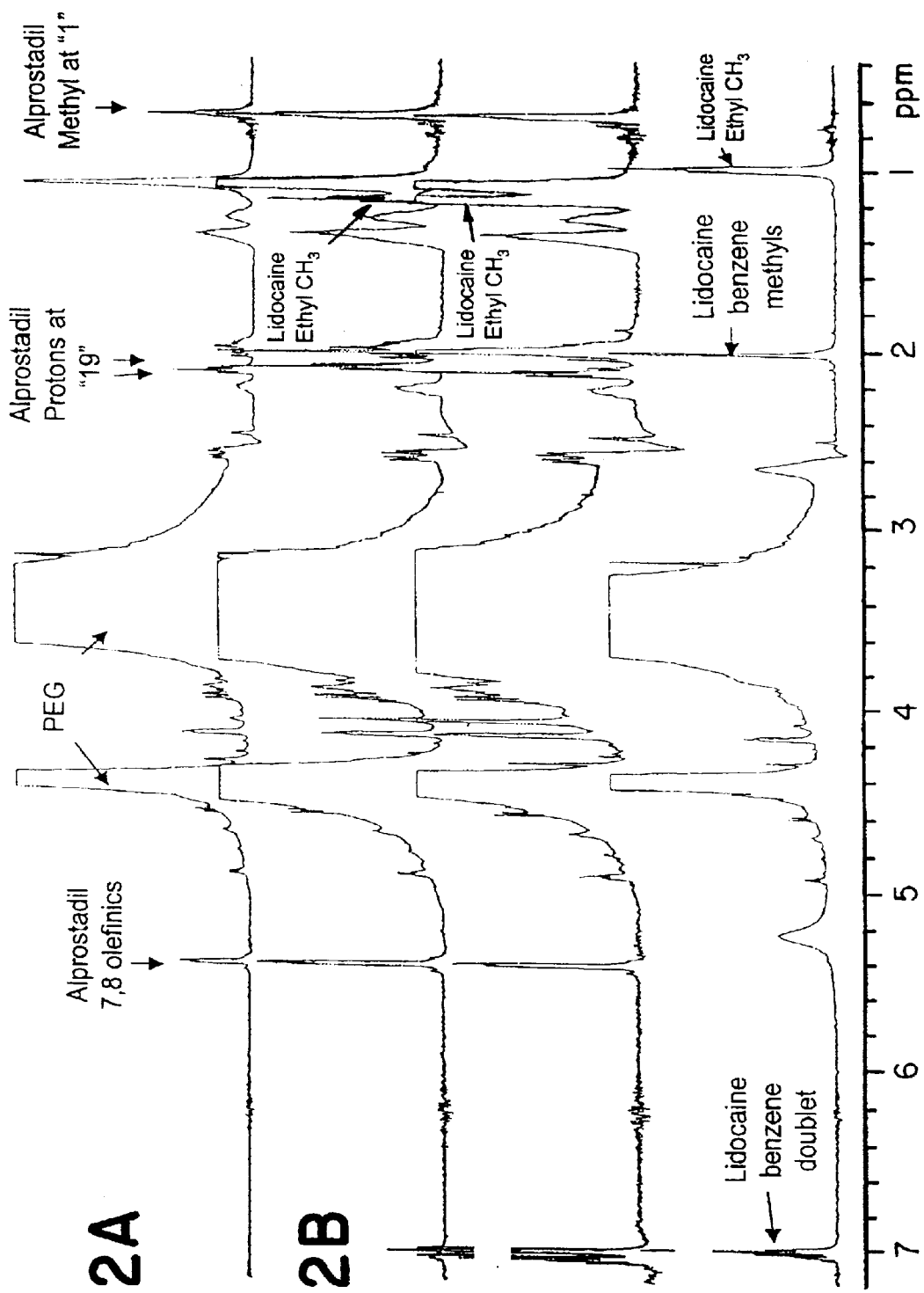
FIG. 2a is the NMR spectrum of alprostadil.
FIG. 2b is the NMR spectrum of lidocaine alprostadilate (alprostadil and lidocaine free base)
FIG. 2c is the NMR spectrum of alprostadil mixed with lidocaine HCl.
FIG. 2d is the NMR spectrum of lidocaine free base.
Figure 3A:
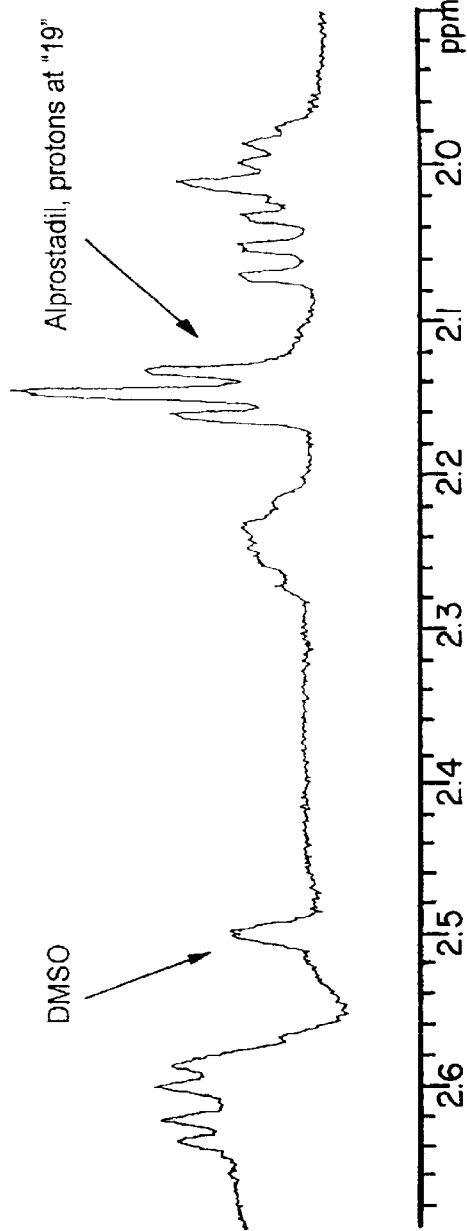
FIG. 3a is an enlarged view of FIG. 1a, showing the NMR spectra of alprostadil.
Figure 3B:
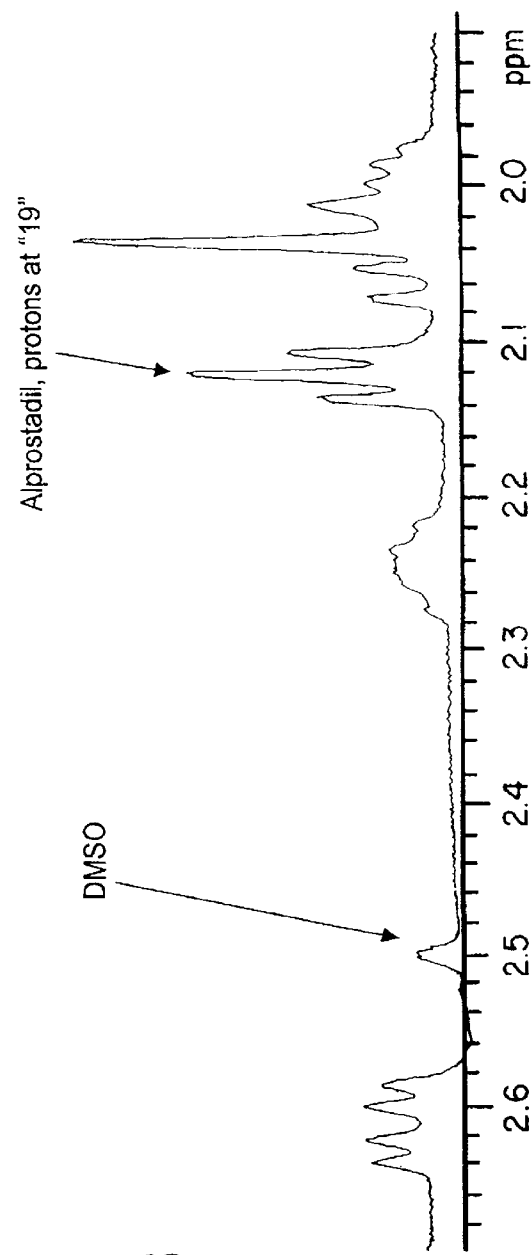
FIG. 3b is an enlarged view of FIG. 1b, showing the NMR spectra of lidocaine alprostadilate.

The compounds of the invention are erection-inducing compounds formed as the stable reaction product of an organic vasoactive cationic moiety, having a positive ionic charge, with an organic vasoactive anionic moiety, having a negative ionic charge. The cationic moiety can also be thought of as a base, the anionic moiety can be thought of as an acid, and the reaction product can be thought of as a "salt" or a "complex."

The organic cation component is selected from any of the following vasoactive compounds as the free base: phentolamine, papaverine , hydralazine, ketanserin, delquamine (delaquamine), trazaodone, yohimbine, linsidomine, molsidomine, ifenprodil, piribedil, dipyramidole, minoxidil, phenoxybenzamine, prazosin, terazocin, doxazocin, sildenafil or moxisylyte (moxisylate), or local anesthetics such as procaine or lidocaine free base.

The organic anion component is selected from any of the following as free acids: vasoactive eicosanoids such as the free acid alprostadil (prostaglandin $E_1$), prostaglandin $E_0$, (13, 14-dihydroprostaglandin $E_1$), dinoprostone (prostaglandin $E_2$), epoprostenol (prostacyclin, $PGI_2$) and other prostaglandins; or other vasoactive anions such as nitroprusside.

The free anion or acid and the free cation or base are mixed, typically in equimolar amounts, in a suitable solvent and the reaction product is crystallized by chilling and adding a solvent or vehicle in which the product is not soluble. Alternatively, the free anion and free cation may be combined in a suitable vehicle for direct use rather than crystallized separately.

Two preferred compounds of the invention are described in detail: lidocaine alprostadilate and prazosin alprostadilate. These compounds are useful for the treatment of erectile dysfunction.

There have been reports that mixtures of alprostadil and local anesthetic agents such as procaine (Schramek, P., et al., *J. Urol.* 1994; 152:1108–1110) and lidocaine (Schouman, M., et al., *J. Urol.* 1992 Oct; 148(4):1266; Kattan, S., *Urology* 1995:Jun:45(6):1032–6) can relieve some of the irritation due to alprostadil upon intracavernosal injection or intraurethral instillation (Wolfson, B., et al., *Urology* 1993; 42:73–5). Lidocaine was used in each study at a concentration of 0.5% (Schouman, M., et al.). Schouman et al. used co-injection of a lidocaine solution to suppress pain due to intracavernosal injection of alprostadil for induction of erection. Kattan administered combinations of solutions of lidocaine and alprostadil by intracavernosal injection in a double-blind fashion and found significant reductions in the pain and an enhancement of erection compared to alprostadil alone. Combinations of solutions of lidocaine and prostaglandin $E_1$ were also used therapeutically to reduce the cardiac side effects of extubation after anaesthesia (Nishina, K., et al., *Can J. Anesth* 1997 Nov; 44(11):1211–14).

None of these reports described the formation of lidocaine or procaine salts of alprostadil.

Oral alpha-blockers have been used in combination with intracavernosal injection of alprostadil (Kaplan, S. A., et al., *Urology* 1998 Nov:52(5):739–43) for the treatment of erectile dysfunction. Oral doxazosin plus intracavernosal alprostadil improved the International Index of Erectile Function (IIEF) score from 36 to 51 compared to intracavernosal alprostadil alone in 38 men with a baseline score of 30 (Kaplan, S. A., et al.). Intraurethral prazosin hydrochloride-alprostadil combinations were shown to be slightly more effective than intraurethral alprostadil alone (Peterson, C. A., et al., *J. Urol.* 1998 May; 159(5); 1523–7) and increased the effectiveness of lower doses of alprostadil. In a separate study, alprostadil and prazosin hydrochloride were found to have no effect on the viability of sperm (Hellstrom, W. J., et al., *J. Urol* 1998 May; 159(5):1559–62).

None of these studies described the formation of salts of prazosin free base and alprostadil.

Lidocaine Alprostadilate

Lidocaine alprostadilate has the following chemical structure (Formula I).

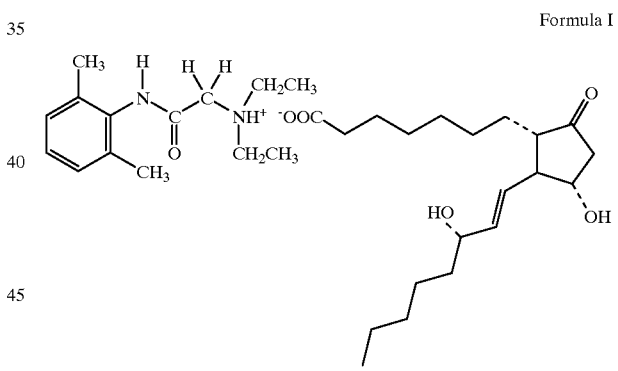

Formula I

Lidocaine alprostadilate has a molecular formula of $C_{34}H_{56}N_2O_6$ and a molecular weight of 322.

Lidocaine alprostadilate is a compound, and is not a mixture of its organic acid and base starting materials. This is shown by nuclear magnetic resonance (NMR) spectra. NMR experiments were performed in the solvent perdeuterodimethylsulfoxide (DMSO) on a Varian Unity Plus 500 spectrometer at 30° C. FIGS. 1a–1e show the proton NMR spectra of alprostadil alone (FIG. 1a), lidocaine alprostadilate (FIG. 1b), a mixture of lidocaine HCl and alprostadil (FIG. 1c), and lidocaine free base alone (FIG. 1d).

Lidocaine alprostadilate may be formed from the reaction of a commercially available lidocaine free base and alprostadil. For example, lidocaine free base (USP) may be dissolved in a solution of alprostadil and a suitable solvent, for example acetone. In a preferred method, lidocaine and alprostadil are added in approximately equimolar amounts. The volume of the solvent may be reduced, for example by contacting the solution with a nitrogen stream. A less polar solvent than the first solvent, for example anhydrous diethyl ether (which is less polar than acetone), may be added and the volume again reduced. Thereafter, lidocaine alprostadilate forms by crystallization. The solution may be cooled to aid in crystallization. The remaining liquids may be decanted and the crystals dried, for example in a vacuum dessicator.

Prazosin Alprostadilate

Another effective therapeutic composition for transurethral induction of erection of the penis is prazosin alprostadilate, which has the following chemical structure (Formula II):

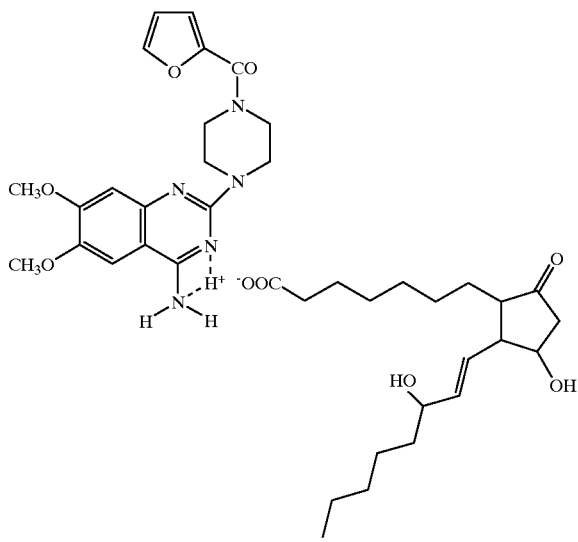

This compound has the molecular formula $C_{39}H_{55}N_5O_9$ and a molecular weight of 737.894.

Figure 5A:
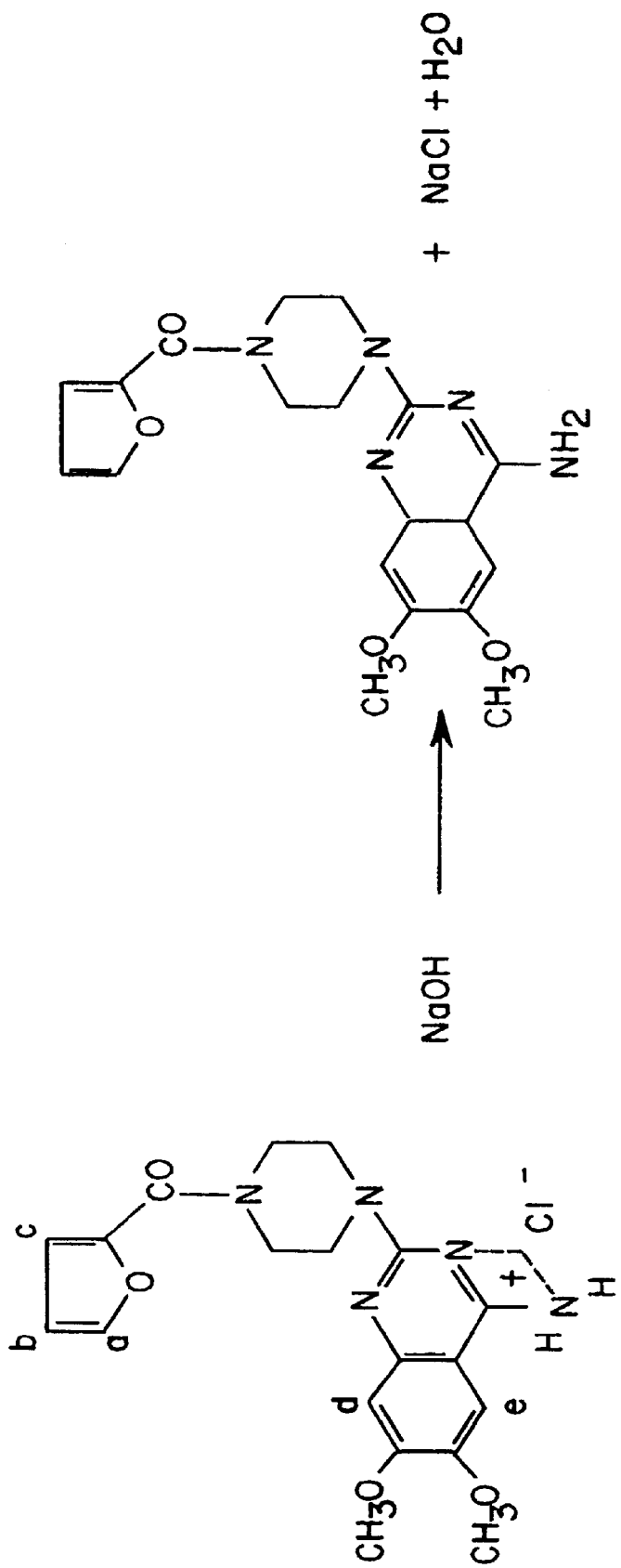
FIGS. 5a and 5b depict a reaction scheme for the formation of prazosin alprostadilate.
Figure 5B:
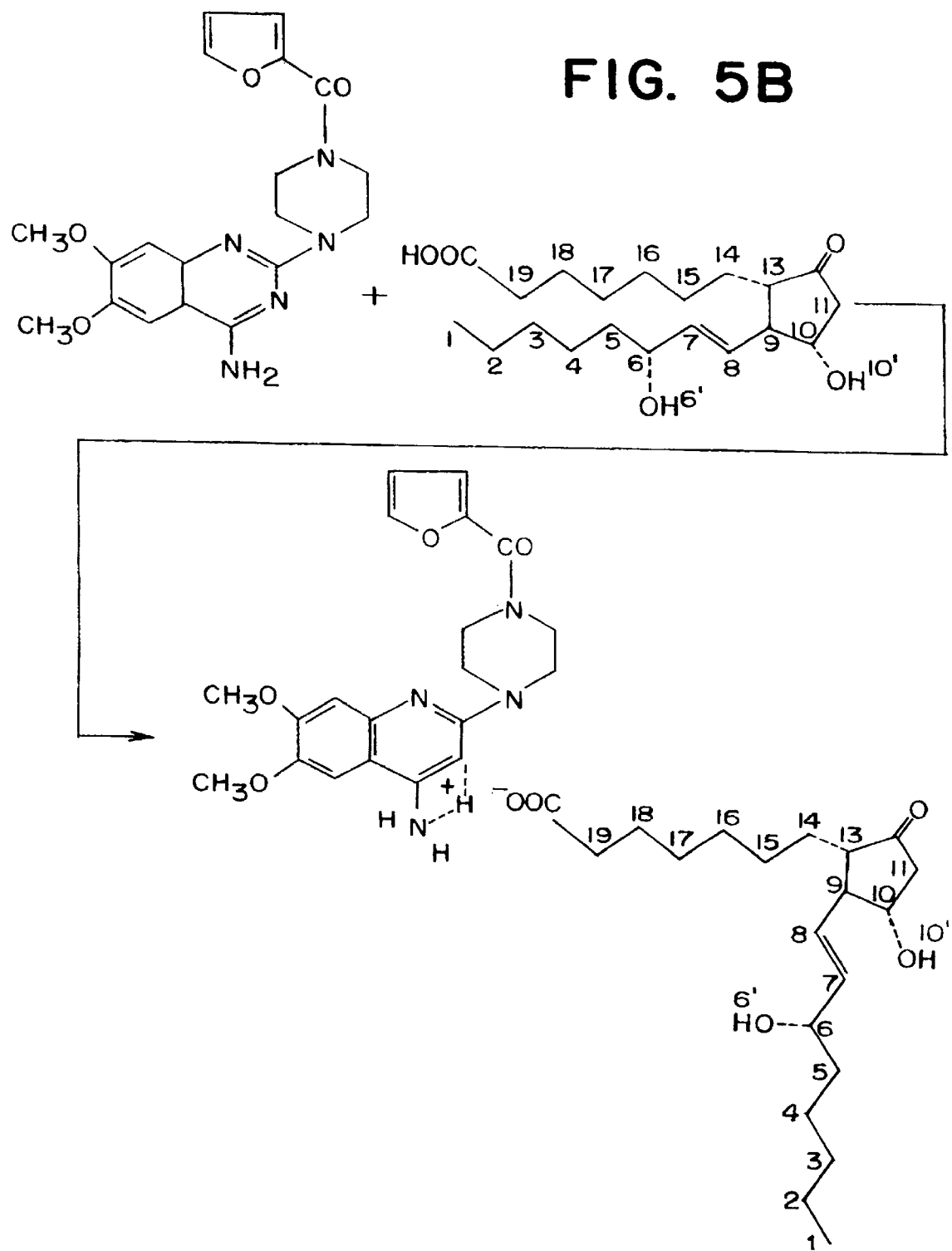

Prazosin alprostidilate may be obtained by the synthesis depicted in FIGS. 5a and 5b. In the method shown in FIG. 5a, prazosin alprostidilate may be formed by a combination of a commercially available prazosin salt other than prazosin alprostidilate (such as prazosin hydrochloride) and alprostadil. In a first method, the prazosin salt is dissolved in a suitable solvent, for example water, to form a first solution. Sodium hydroxide may be added, and a prazosin free base is allowed to crystallize from the first solution. Crystallization may be aided by cooling. Pellets are formed upon centrifugation. The solution may be chilled, and prazosin free base pellets are formed and dried. The pellets are then dissolved in a suitable solvent, for example a solvent comprising acetonitrile and water, to form a second solution. Alprostadil, preferably in a roughly equimolar amount to the prazosin, is added to the second solution. The second solution may thereafter be heated, for example up to about 50° C. The volume may be reduced, for example by contacting the second solution with a nitrogen stream to remove the solvent. As the amount of solvent decreases, white crystals appear. The remaining liquor may be decanted and the solvents removed and dried, for example in a vacuum dessicator.

In the method shown in FIG. 5b, prazosin alprostidilate may be formed without formation of the intermediate prazosin free base as a solid. In this method, a commercially available prazosin salt other than prazosin alprostidilate (for example, prazosin hydrochloride) is dissolved in polyethylene glycol, preferably having a molecular weight of about 400 daltons. The preparation of the solution preferably occurs at room temperature. An alkali hydroxide (for example sodium hydroxide or potassium hydroxide), preferably in an approximately equimolar amount to the prazosin, is added to the polyethylene glycol solution. The resulting composition may be mixed and the solution dried, for example by the addition of phosphorous pentoxide. The composition may then be mixed with alprostadil, and prazosin alprostadilate forms, as has been shown by NMR spectroscopy.

Pharmaceutical Formulations

The invention is also directed to pharmaceutical compositions or formulations comprising either lidocaine alprostidilate or prazosin alprostidilate and a pharmaceutically acceptable carrier or diluent. In certain embodiments, the invention is directed to pharmaceutical compositions comprising both lidocaine alprostidilate and prazosin alprostidilate.

The formulations of the present invention can be solutions, suspensions, emulsions, syrups and the like. The compositions may contain a suitable carrier, diluent, or excipient, such as a medium chain triglyceride oil or magnesium stearate. In preferred formulations, a medium chain triglyceride oil and magnesium stearate are present in an approximately 1:1 ratio. Standard texts, such as *Remington's Pharmaceutical Science,* 18th Ed., 1990, incorporated herein by reference, may be consulted to prepare suitable preparations, without undue experimentation.

A preferred carrier is polyethylene glycol (PEG). More preferred is a mixture of polyethylene glycol having a high molecular weight, for example of greater than 900 (most preferably, about 1,000), and polyethylene glycol having a low molecular weight, for example of less than 500 preferably about 400). Preferred ratios of low molecular weight PEG to high molecular weight PEG are approximately 1:1 to 1:5, more preferably about 1:2.

A particularly preferred carrier is PEG in the ratio of about one part PEG with a MW of 100 to about two parts PEG with a MW of about 400.

Preferred emulsifiers include phosphatidylcholine emulsifiers, such as dilauroylphosphatidylcholine.

The formulations can include powdered carriers, such as lactose, sucrose, mannitol, starch, cellulose derivatives, xanthum gum, magnesium stearate, stearic acid, and the like.

The composition may also comprise a penetration enhancer. Suitable penetration enhancers include glycerol, glycerol monolaureate, dimethyl sulfoxide or oils, such as a mineral oil or medium chain triglyceride oil.

Antioxidants such as, for example butylated hydroxytoluene (BHT), sodium bisulfate, sodium sulfite, sodium EDTA, ascorbic acid, and the like can be used either alone or in combination with other suitable antioxidants or stabilizing agents typically employed in pharmaceutical compositions.

The formulations can also include any of the commonly used disintegrants, lubricants, plasticizers, colorants, and dosing vehicles. Suitable pharmaceutical carriers are described in *Remington's Pharmaceutical Sciences,* a standard reference text in this field. Suitable formulations typically contain from about 1 to about 1000 mg of active ingredient per dosage unit. In these pharmaceutical compositions, the active ingredient will ordinarily be present in an amount of about 0.5 to about 95%, by weight, based on the total weight of the composition.

The magnitude of the therapeutic dose of the compounds of the invention will vary with the nature and severity of the condition to be treated and with the particular route of administration.

The compositions include compositions suitable for topical (including transdermal devices, aerosols, creams, ointments, lotions and dusting powders), or intraurethral administration, for example by instillation. Although the most suitable route in any given case will depend largely on the nature and severity of the condition being treated and on the nature of the active ingredient, the compositions of the invention may be conveniently presented in unit dosage form and prepared by any of the methods well known in the art of pharmacy.

In preferred embodiments, the pharmaceutical composition is in the form of an intraurethral formulation, such as a formulation which can be instilled into the penis with a catheter or an applicator. The pharmaceutical formulations of the invention may be formed by first preparing the prazosin alprostadil and/or lidocaine alprostadil, then adding a pharmaceutically acceptable carrier, and other ingredients, such as emulsifiers, buffering agents, adjuvants, preservatives, penetration enhancing agents and gelling or viscosity agents. The formulation may be cooled and formed into a paste, which may then be mixed with a suitable solvent, for example water, and then administered.

EXEMPLARY EMBODIMENTS OF THE INVENTION

EXAMPLE 1

Synthesis of Lidocaine Alprostadilate

Lidocaine alprostadilate was synthesized as depicted in FIG. 1, as follows: 50 mg alprostadil (Chinoin Chemical Works, Budapest, Hungary) were dissolved in 1.5 ml acetone (Optima, Fisher Chemical Company). To the solution was added 33.05 mg lidocaine USP, (Spectrum Quality Products, Gardena, Calif.) and the solids dissolved by vortexing. The volume of acetone was reduced to approximately one-third under a nitrogen stream at room temperature and anhydrous diethyl ether (J. T. Baker) was added to make a total volume of 1.5 ml again. Volume was again reduced under a nitrogen stream and crystallization was soon evident. When the volume had been reduced to approximately one-third the starting volume, remaining mother liquor was decanted and the crystals placed in a vacuum desiccator containing phosphorus pentoxide for three days.

After desiccation, crystals were sent for elemental analysis (Galbraith Laboratories, Knoxville, Tenn.) assuming the empirical formula $C_{34}H_{56}N_2O_6$ and showed (theoretical; observed) C 69.35%; 69.26%, H 9.59%; 9.60%, N 4.76%; 4.75%, O 16.30%; 16.07%. The pH of a 10 mM aqueous solution of lidocaine alprostadilate was 6.29–6.36 at 22° C. The melting point of the crystals was 51–53° C. The ultraviolet spectrum in methanol had maxima at 205 nm ($\epsilon$=1120), 229 nm ($\epsilon$=1232) and 264 nm ($\epsilon$=255). The infrared spectrum in Nujol demonstrated absorbance at 3375, 1731 and 1662 $cm^{-1}$ consistent with hydroxyl, carboxyl and CONH groups, respectively.

EXAMPLE 2

NMR Spectra

Solutions of alprostadil (a), lidocaine free base (d), and equimolar mixtures of alprostadil and lidocaine free base (b) or lidocaine hydrochloride (c) in a solution containing polyethylene glycol in polyethylene glycol were formed and NMR spectra were obtained and are shown in FIGS. 2a–2d, 3a and 3b. When NMR spectra were obtained in deuterated DMSO alone (not shown), there were no chemical shifts attributable to formation of an ionic bond, however, in a solvent of deuterated DMSO, water as $d_2O$ and 400 dalton PEG 1:6:3, ionization occurred as shown by the up field shift of the triplet assignable to the protons in position "19", nearest the ionic bond on the alprostadilate molecule as shown in Reaction 3. This 0.03 ppm shift from 2.15 ppm to 2.12 ppm, shown in close-up in FIG. 2, indicates increased electron shielding due to formation of the ionic bond at the neighboring carboxyl group. This up field shift did not occur in the same solvent system when equimolar alprostadil and lidocaine hydrochloride were mixed, as shown in FIG. 1c, because ionic interaction between lidocaine hydrochloride and alprostadil was prevented by the presence of chloride ion. Corresponding downfield shifts in the resonances of the methyl protons on the N,N-diethyl groups are seen: in FIG. 1d, lidocaine free base shows these resonances at 1 ppm, but in FIGS. 1b and 1c, the ionic effect of alprostadil and chloride, respectively, shift these resonances due to deshielding to 1.2 ppm. Analogous effects in the N,N-diethyl ethyl protons are obscured by the polyethyleneglycol resonances.

These NMR findings demonstrate that lidocaine alprostadilate exists as a detectable chemical entity in polyethylene glycol-water solvent systems such as exist during the suggested medical use of the compound.

EXAMPLE 3

Medical use of Lidocaine Alprostadilate

A pharmaceutical preparation of lidocaine alprostadilate was made as follows: 50 mg of alprostadil USP (Chinoin Chemical Works, Sanofi Synthelabo, Budapest, Hungary) was dissolved at 60° C. in an agate mortar and pestle in 1892 mg of a liquid mixture of polyethylene glycol 1000 MW: 400 MW 2:1 (Paddock Laboratories, Minneapolis, Minn.) containing 0.02% butylated hydroxytoluene. To this was added an amount of lidocaine free base equimolar to the alprostadil: 33.05 mg lidocaine USP (Spectrum Quality Products, Gardena, Calif.). Then, 10 mg phentolamine mesylate, and 20 mg dilauroylphosphatidylcholine (Avanti Polar Lipids, Alabaster, Ala.) were added and mixed. This solution was sterilized by filtration through a 0.2 micron anodized aluminum filter (Anotop 25, Whatman International, Maidstone, England) by syringe at 55° C. and 350 microliter aliquots were directly dispensed into 500 microliter luer-lok gastight syringes (Hamilton) in which the inner diameter of the Teflon luer assembly had been drilled to the same inner diameter as the catheters described below.

On cooling to room temperature, the composition solidified to a white paste. The pH of the paste when mixed with an equal mass of distilled water, was 6.95–7.02. The 500 microliter syringes were graduated in 17.5 and 35 microliter volumes. On the luer-lok end was fitted a 2 cm catheter made from extruded polyethylene tubing with an outer diameter equivalent to 8 French and an inner diameter of 0.050 inches. The catheters were made by Custom Medical Concepts, Chelmsford, Mass. The catheters were open at both ends and rounded at the distal end into an atraumatic shape known in the art. The proximal end was fitted with a low-dead-volume female luer to 1/16 barb adapter made of KYNAR, which is a hard, white polyvinylidene fluoride resin known for its resistance to chemical erosion and heat. The luer is available from Value Plastics in Fort Collins, Colo. It is designed so that there is no constriction in the inner diameter of the applicator at any point in the path of the extruded composition.

Prior to installation on the 500 microliter syringes, the catheters were sealed in suitable packaging required for ethylene oxide sterilization and then sterilized. In use, the subject first urinated to provide residual moisture in the urethra. The catheter tip was inserted about 1 cm into the urethra and a dose of 40 milligrams of composition, containing 1000 mg of alprostadil, 200 mg of phentolamine mesylate and 660 micrograms of lidocaine was dispensed by moving the plunger of the syringe the distance equivalent to 35 ml, or, half of that dose was dispensed by depressing the plunger half that distance.

Figure 4:
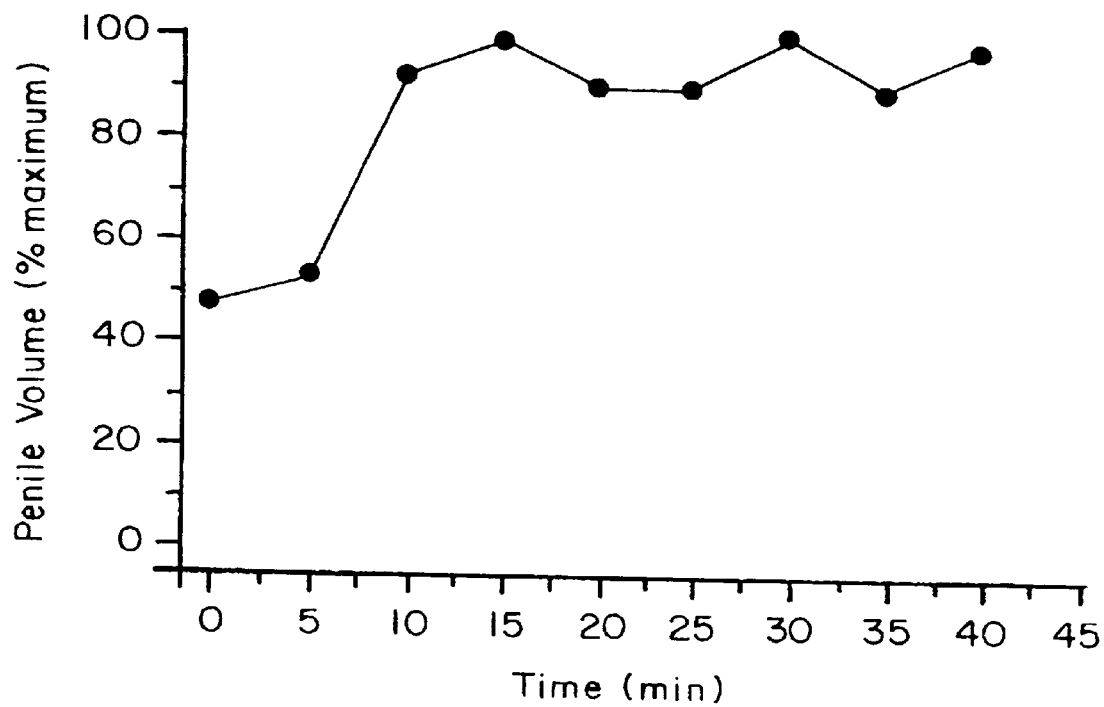
FIG. 4 depicts the results of percent maximum of penile volume for a lidocaine alprostadilate composition of the invention.

Results are shown in FIG. 4 from an unaroused human subject who had taken 25 mg sildenafil citrate (Viagra, Pfizer) by mouth one-half hour before use.

EXAMPLE 4

Synthesis of Prazosin Alprostadilate

Prazosin alprostadilate was synthesized as follows. Of prazosin hydrochloride (Sigma), (202.2 mg) were dissolved in 300 cc sterile water (Baxter). To the solution was added 481.5 $\mu$L of 1 M sodium hydroxide (Fisher). The solution slowly became cloudy as it was chilled for 1 hour on ice. The cloudy solution was transferred to conical tubes in order to hasten precipitation by centrifugation at 1000 g for 5 minutes. Pellets were consolidated and recentrifuged. The pellet was resuspended in 10 cc sterile water, and after centrifugation, the supernatant was discarded and the pellet dried for 2 days in a vacuum desiccator containing phosphorus pentoxide. In 5 cc of a solution of 4:1 acetonitrile and water, 46.5 mg prazosin free base and an equimolar amount of alprostadil, 43 mg, were dissolved by heating to 50° C. for 5 minutes. The volume was reduced by one-half under a stream of nitrogen and acetonitrile was added to increase the volume 50%. This was repeated until water was removed azeotropically and only acetonitrile remained. As the volume of acetonitrile decreased, white crystals appeared. The mother liquor was decanted and discarded. The crystals were dried in a vacuum dessicator containing phosphorus pentoxide.

The melting point of the crystals was 160–165° C. The crystals were sent for elemental analysis (Galbraith Laboratories, Knoxville, Tenn.) assuming the empirical formula $C_{39}H_{55}N_5O_9$ with a molecular weight of 737.894 daltons and showed (theoretical; observed) C 63.48%; 62.83%, H 7.51%; 7.69%, N 9.49%; 9.40%, O 19.51%; 18.63%. The pH of a 10 mM aqueous solution of prazosin alprostadilate was 6.32–6.38 at 22° C. The ultraviolet spectrum in methanol had maxima at 214 nm (log $\epsilon$=4.307), 230 nm (log $\epsilon$=4.317), 240 nm (log $\epsilon$=4.332), 249 nm (log $\epsilon$=4.352) and 341 nm (log $\epsilon$=3.799). The infrared spectrum in Nujol demonstrated absorbance at 3404 ($NH_2$), 3327 (OH), 3211 ($NH_2$), 2856 ($CH_3O$), 1730 (COO), 1622 and 1559 ($NH_3+$) and 1376 $cm^{-1}$ (COO).

EXAMPLE 5

NMR Spectra

Figure 6A:
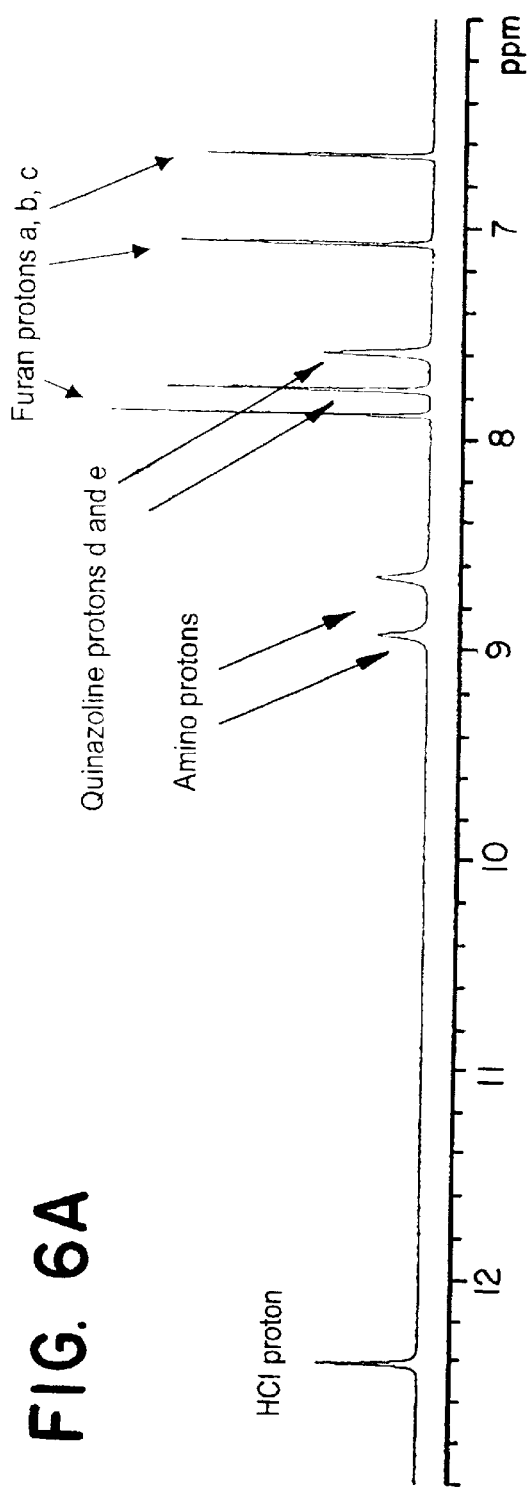
FIG. 6a depicts the NMR spectra of prazosin hydrochloride in deuterated DMSO.
Figure 6B:
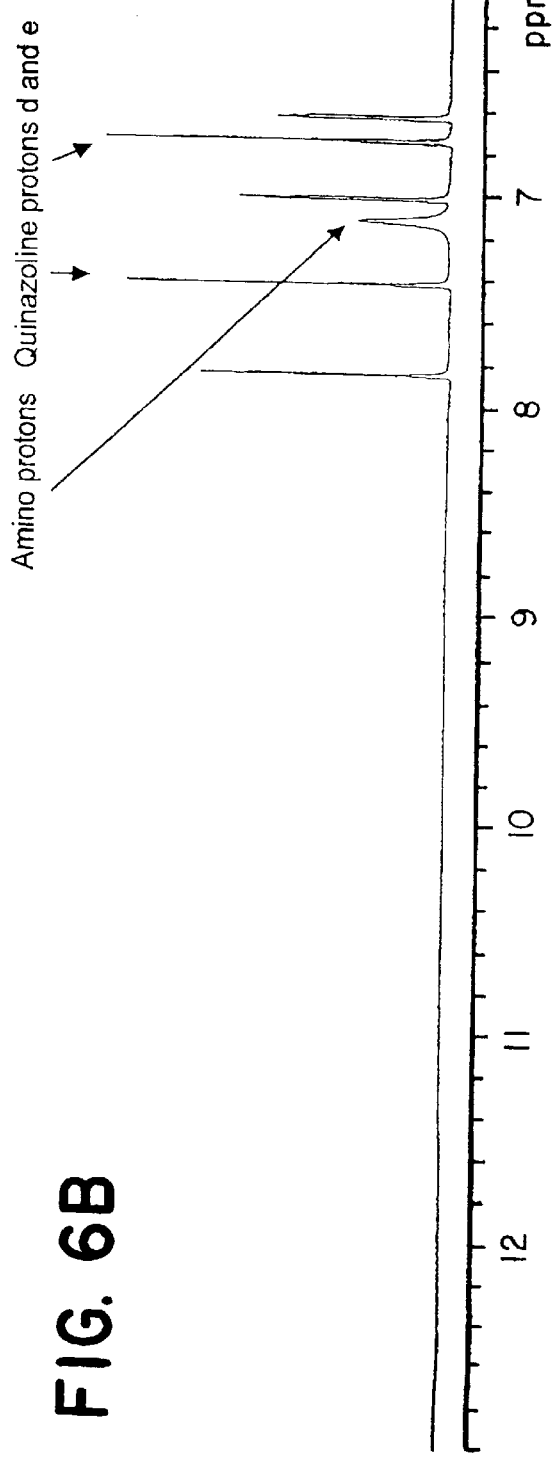
FIG. 6b depicts the NMR spectra of prazosin free base in deuterated DMSO.
Figure 9A:
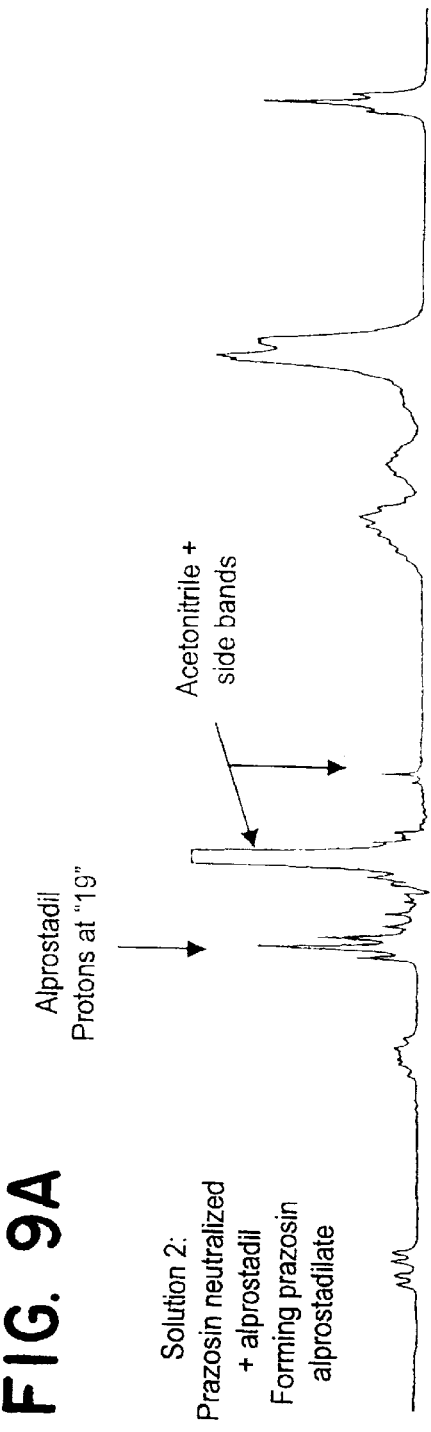
FIG. 9a is an enlarged view of FIG. 8b, showing the NMR spectra of prazosin HCl and NaOH in PEG and alprostadil.
Figure 9B:
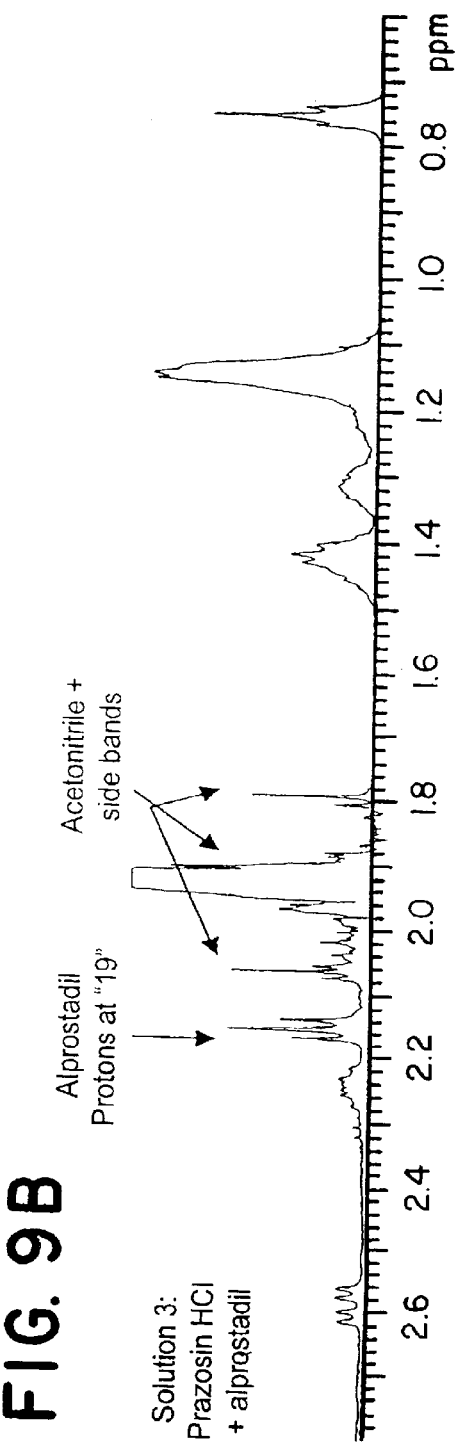
FIG. 9b is an enlarged view of FIG. 8c, showing the NMR spectra of prazosin HCl in PEG and alprostadil.

The NMR spectra of prazosin hydrochloride in deuterated DMSO (FIG. 6*a*) and prazosin free base (FIG. 6*b*) were obtained and compared. In this non-aqueous solvent, the hydrochloride proton was clearly seen at 12.4 ppm and was distinct from the primary amine protons which were split and widely separated at 8.8 and 9.0 ppm in the hydrochloride, but a single resonance at 7.2 ppm in the free base. This indicated that the site of protonization, by acids such as hydrogen chloride or alprostadil, was as illustrated in FIGS. 5(*a*) and 5(*b*), allowing resonance in a ring-like structure involving one of the primary amine protons and conferring a partial $NH_3+$ structure as suggested by the IR spectrum mentioned above. This site of protonization on the ring nitrogen was further supported by the large shifts of the resonances for the quinazoline protons d and e by induction through the aromatic system. In FIGS. 6(*a*) and 6(*b*), protonization by hydrochloride can be seen to shift these resonances, labeled d,e downfield, consistent with deshielding, or removal of electrons from the aromatic rings by ionization of the ring nitrogen as indicated in FIGS. 5(*a*) and 5(*b*). Comparison of these resonances in FIGS. 6(*a*)–6(*d*), in a solvent of deuterated DMSO, water as $d_2O$ and 400 dalton PEG 1:6:3, shows that the deshielding is of a greater magnitude when ionization is due to hydrochloride (7(*c*) and 7(*d*)), than when ionization is due to alprostadil 7(*b*). FIGS. 7(*a*)–7(*d*) also show the up field shift of the triplet assignable to the protons in position "19", nearest the ionic bond on the alprostadilate molecule as shown in FIGS. 5(*a*) and 5(*b*). This 0.1 ppm shift from 2.15 ppm to 2.05 ppm indicates increased electron shielding due to formation of the ionic bond at the neighboring carboxyl group. This up field shift did not occur in the same solvent system when equimolar alprostadil and prazosin hydrochloride were mixed, as shown in FIG. 7(*c*), indicating that the presence of the chloride anion prevents interaction of prazosin with alprostadil.

EXAMPLE 6

Syntheses of Prazosin Alprostadilate and NMR Spectra

The synthesis of prazosin alprostidilate was carried out in polyethylene glycol according to the method depicted in FIG. 5(b), except prazosin free base was not isolated as a separate crystalline intermediate between the steps of FIG. 5(a) and FIG. 5(b): Of prazosin hydrochloride USP (Fermion, Orion Corp, Espoo, Finland) 174.5 mg was dispersed in 10 g of 400 dalton (liquid at room temperature) polyethyleneglycol (Paddock Labs, Minneapolis, Minn.) in an agate mortar and pestle. A pellet of sodium hydroxide (Fisher) was crushed and an equimolar amount, 16.62 mg, was added to the prazosin HCl. The solution slowly clarified over 30 minutes of mixing at room temperature. The solution was dried in a vacuum desiccator over phosphorus pentoxide to remove water formed in the reaction of sodium hydroxide and prazosin hydrochloride. This comprised Solution 1 for the NMR studies below.

Of the prazosin-sodium hydroxide solution in polyethyleneglycol, 1 g was measured into an agate mortar and pestle and an equimolar amount of alprostadil USP (Chinoin Chemical Works, Sanofi ynthelabo, Budapest, Hungary), 14.73 mg, was added and mixed. The alprostadil readily dissolved at room temperature with gentle mixing. This comprised Solution 2 for NMR studies below.

Of prazosin hydrochloride USP (Fermion, Orion Corp, Espoo, Finland) 174.5 mg was dispersed in 10 g of 400 dalton (liquid at room temperature) polyethyleneglycol (Paddock Labs, Minneapolis, Minn.) in an agate mortar and pestle. To 1 g of this solution was added an equimolar amount of alprostadil, 14.73 mg. This comprised Solution 3 for the NMR studies described below.

The solution remained cloudy white despite mixing. Solution 3 with no added alprostadil comprised Solution 4 for NMR studies below.

For NMR studies, the polyethylene glycol Solutions 1–4 above were prepared as follows. The exchangeable protons of polyethylene glycol were exchanged with deuterium by repeated addition of two volumes of deuterium oxide and its azeotropic evaporation by addition of acetonitrile under a nitrogen stream at 60° C. When the original volume of Solutions 1–4 was restored, equal volumes of deuterium oxide and deuterated acetonitrile were added. All of the solutions clarified with gentle mixing.

FIGS. 8(a)–8(d) and 9 show the results of NMR studies of Solutions 1–4. FIGS. 8(a)–8(d) show the proton NMR spectra obtained on the Varian Unity Plus 500 with a proton resonance frequency of 500 MHz at 30° C. FIG. 8(a) shows prazosin HCl neutralized with sodium hydroxide in 400 dalton polyethylene glycol. The spectrum is consistent with a single chemical entity most resembling the prazosin free base of FIG. 5 (bottom), indicating complete titration of the prazosin HCl by addition of an equimolar quantity of sodium hydroxide in polyethylene glycol. Resonances of the quinazoline protons d and e, connected by dotted lines, can be seen to be furthest upfield of any of the four spectra. In FIG. 8(b), addition of alprostadil shows interaction between the alprostadil and prazosin free base: there are changes consistent with an ionic interaction on both molecules. Aromatic quinazoline protons d and e of prazosin can be seen to be shifted downfield relative to the free base of FIG. 8(a), indicating deshielding by inductive effects of protonization of a ring nitrogen. Correspondingly, the resonances of the alprostadil protons in position "19" of FIG. 5(b) are shifted upfield relative to their position in FIG. 8(c), indicating increased electron density at the neighboring carboxylic acid group. In FIG. 8(c), a mixture of prazosinhydrochloride and alprostadil shows no changes in the aromatic quinazoline protons d and e compared to the prazosin hydrochloride alone in FIG. 8(d) in which the stronger acid, hydrochloride, produces the furthest downfield shift of these protons. FIG. 8 shows the region of 0.6 to 2.8 ppm of the spectra of FIGS. 8(b) and 8(c). The resonances of the protons at alprostadil position "19" from FIG. 5(b) can be seen shift from 2.154ppm in the mixture with prazosin hydrochloride (bottom) to 2.065 ppm due to formation of prazosin alprostadilate (top). This indicates that the new composition of matter, prazosin alprostadilate can be synthesized in polyethylene glycol solution by mixing generic pharmaceuticals and a pharmaceutical-grade neutralizing agent, sodium hydroxide, in the sequence described above.

EXAMPLE 7

Prazosin Alprostadilate and Lidocaine Alprostadilate Intraurethral Treatment

The prazosin free base in polyethylene glycol in Example 6 above was used in the compounding of an intraurethral treatment for erectile dysfunction. Of the above polyethylene glycol solution, 630.3 mg were mixed with 1260.6 mg 1000 dalton polyethylene glycol to give a 2:1 mixture. This was warmed to 50° C. and the following were added to the solution in an agate mortar and pestle: 50 mg alprostadil (Chinoin Chemical Works, Budapest, Hungary), 27 mg lidocaine USP (Spectrum Quality Products, Gardena, Calif.) such that the molarity of the prazosin free base plus that of the lidocaine free base equaled the molarity of the alprostadil. To this solution, 20 mg dilauroylphosphatidylcholine (Avanti Polar Lipids, Alabaster, Ala.) was added and mixed. This was sterilized by filtration through a 0.2 micron anodized aluminum filter (Anotop 25, Whatman International, Maidstone, England) by syringe at 55° C. and 1 g aliquots were directly dispensed into 3 cc luer-lock disposable syringes. On cooling to room temperature, the composition solidified to a white paste.

At the time of use, the luer-lock end was fitted a 2 cm catheter made from extruded polyethylene tubing with an outer diameter equivalent to 8 French and an inner diameter of 0.050 inches. The catheters were made by Custom Medical Concepts, Chelmsford, Mass. The catheters were open at both ends and rounded at the distal end into an atraumatic shape known in the art. The proximal end was fitted with a low-dead-volume female luer to $\frac{1}{16}$ barb adapter made of KYNAR, which is a hard, white polyvinylidene fluoride resin known for its resistance to chemical erosion and heat. The luer is available from Value Plastics in Fort Collins, Colo. It is designed so that there is no constriction in the inner diameter of the applicator at any point in the path of the composition. Prior to installation on the 3 cc disposable syringes, the catheters were sealed in suitable packaging required for ethylene oxide sterilization and then sterilized.

At room temperature, the composition was easily dispensed into the catheter by gently depressing the plunger of the 3 cc disposable syringe. Upon filling to a line inscribed on the catheter, the catheter contained a dose of 40 mg of composition, containing 1000 μg of alprostadil, 200, μg of prazosin and 540, μg of lidocaine. The catheter was then transferred to a disposable 1 cc tuberculin syringe with the plunger withdrawn to admit about 300 μL of air.

A normal male subject urinated, then the catheter tip was inserted about 1 cm into the urethra and its contents were dispensed by depressing the plunger of the tuberculin syringe completely. The contents were instilled into the urethra by the compressed air, attended by an audible "pop". The medication was distributed along the penile urethra by holding the glans closed and briefly massaging the liquid proximally.

In the absence of sexual arousal, fall erection was attained in about 7 minutes. The subject was familiar with the effects of MUSE due to prior use. Asked to rate the degree of acute irritation compared to MUSE, the subject rated the new formulation less irritating than MUSE. Asked to rate the degree of later onset penile aching, the subject rated the degree of aching less with the new composition than with MUSE.

EXAMPLE 8

Delivery System and Dosage Form Packaging

In one embodiment, the composition according to the invention is delivered into the penis by an applicator. An exemplary applicator is made by Custom Medical Concepts, Chelmsford, Mass., from extruded polyethylene catheter tubing in an outer diameter equivalent to 8 French and inner diameter of 0.050 inches. This applicator is open at both ends and rounded at the distal end into an atraumatic shape known in the art. The proximal end was fitted with a low-dead-volume female luer to 1/16 barb adapter made of KYNAR, which is a hard, white polyvinylidene fluoride resin known for its resistance to chemical erosion and heat. The applicator is designed so that there is no constriction in the inner diameter of the applicator at any point in the path of the composition. The luer is available from Value Plastics in Fort Collins, Colo. The applicators are sealed in suitable packaging required for ethylene oxide sterilization and then sterilized.

Prior to packaging, the composition is passed through a warmed, sterile, 0.2 micron anodized aluminum filter (Anotop 10, Whatman International, Maidstone, England). Premeasured single-use applicators were prepared by drawing up the warmed composition to give the approximate dosages as shown below. Each applicator contained one of the following dosage combinations as marked.

TABLE II

| Marking | Alprostadil (μg) | Lidocaine (μg) | Prazosin (μg) | Total Composition (mg) |
|---|---|---|---|---|
| 250 | 250 | 135 | 50 | 10 |
| 500 | 500 | 270 | 100 | 20 |
| 750 | 750 | 405 | 150 | 30 |
| 1000 | 1000 | 540 | 200 | 40 |

Alternatively, the composition is passed through a warm, sterile, 0.2 micron anodized aluminum filter (Anotop 10, Whatman, International, Maidstone, England) into a 3 cc syringe or dispenser. The dispenser was previously sterilized by ethylene oxide and lubricated with 200 MW polyethylene glycol containing 0.005% BHT. The dispenser was filled with the composition in a laminar flow hood and inserted and sealed into a sterile wrapper.

The applicator was then fitted onto the dispenser and the composition was expressed into the applicator to a proximal mark, for a dose of 500 micrograms of alprostadil equivalent and to a distal mark on the dispenser for 1000 micrograms. The loaded applicator was then detached from the dispenser and attached to a 1 cc syringe. The dispenser-applicator apparatus allowed variable doses to be measured out by the user according to his requirements at the time of use.

In use, the subject first urinated, then the applicator was inserted one inch or less into the urinary meatus, and the composition was deployed by forced air through the syringe by pushing the plunger. Delivery of the effective dose was attended by an audible "pop". The concentrations of the new compositions of matter and emulsifier in the composition were chosen to prevent overdosage at the holding capacity of the human urethra. That is, the concentration of active ingredients in the vehicle was diluted to a point such that the maximum capacity of the urethra would contain a safe dose of active ingredients effectively preventing overdosage. This is in contrast to the prior art compositions which are many times more concentrated and many times the recommended dosage may be injected and held within the urethra.

Although illustrative embodiments are disclosed, other suitable embodiments for practicing the invention may be employed and will be apparent to persons of ordinary skill in the art. The particular compounds, production methods and treatments disclosed are exemplary, and it is to be understood that the scope of the invention is to be determined according to the claims.

I claim:

1. A compound of Formula I:

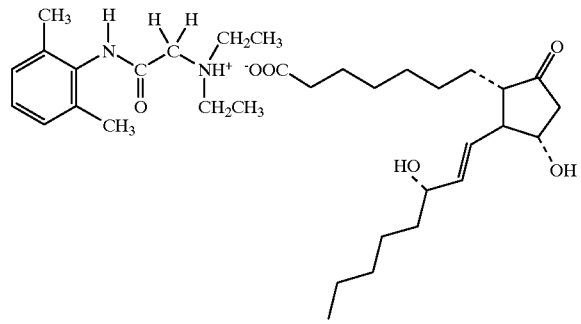

2. A pharmaceutical composition comprising a compound of claim 1 and a pharmaceutically acceptable carrier.

3. A pharmaceutical composition of claim 2, further comprising an emulsifier.

4. A pharmaceutical composition of claim 3, wherein said emulsifier is a phosphatidylcholine compound.

5. A pharmaceutical composition of claim 4, wherein said phosphatidylcholine compound is dilauroylphosphatidylcholine.

6. A pharmaceutical composition of claim 3, wherein said carrier is polyethylene glycol.

7. A pharmaceutical composition of claim 6, wherein said polyethylene glycol is present in a ratio of about two parts polyethylene glycol having a molecular weight of about 1000 to about one part polyethylene glycol having a molecular weight of about 400.

8. A pharmaceutical composition of claim 3, further comprising butylated hydroxytoluene.

9. A pharmaceutical composition of claim 3, further comprising a penetration enhancer selected from the group consisting of glycerol, glycerol monolaureate, dimethyl sulfoxide, mineral oil, and a medium chain triglyceride oil.

10. A compound of Formula II:

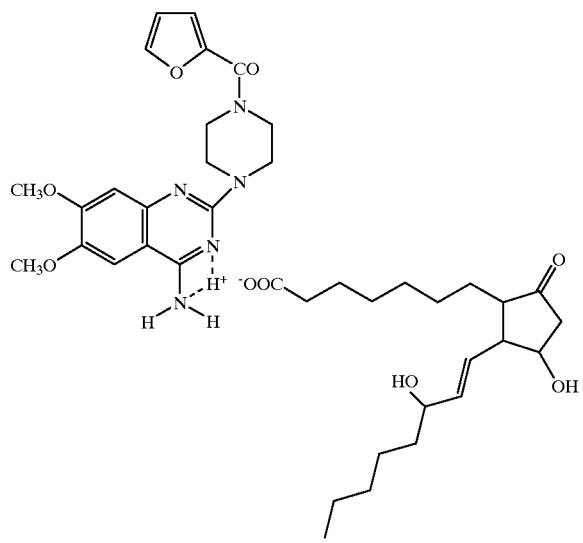

11. A pharmaceutical composition comprising a compound of claim 10 and a pharmaceutically acceptable carrier.

12. A pharmaceutical composition of claim 11, further comprising an emulsifier.

13. A pharmaceutical composition of claim 11, wherein said emulsifier is a phosphatidylcholine compound.

14. A pharmaceutical composition of claim 13, wherein said phosphatidylcholine compound is dilauroylphosphatidylcholine.

15. A pharmaceutical composition of claim 11, wherein said carrier is polyethylene glycol.

16. A pharmaceutical composition of claim 15, wherein said polyethylene glycol is present in a ratio of about two parts polyethylene glycol having a molecular weight of about 1000 to about one part polyethylene glycol having a molecular weight of about 400.

17. A pharmaceutical composition of claim 13, further comprising butylated hydroxytoluene.

18. A pharmaceutical composition of claim 11, further comprising a penetration enhancer selected from the group consisting of glycerol, glycerol monolaureate, dimethyl sulfoxide, mineral oil, and a medium chain triglyceride oil.

\* \* \* \* \*